(12) United States Patent
Hashimoto

(10) Patent No.: US 8,723,921 B2
(45) Date of Patent: May 13, 2014

(54) IMAGE PICKUP SYSTEM

(71) Applicant: Olympus Medical Systems Corp., Tokyo (JP)

(72) Inventor: Hidenori Hashimoto, Sagamihara (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/903,388

(22) Filed: May 28, 2013

(65) Prior Publication Data

US 2013/0300847 A1    Nov. 14, 2013

Related U.S. Application Data

(63) Continuation of application No. PCT/JP2012/083452, filed on Dec. 25, 2012.

(30) Foreign Application Priority Data

Mar. 1, 2012   (JP) .................................. 2012-045824

(51) Int. Cl.
*H04N 7/18*    (2006.01)
(52) U.S. Cl.
USPC ............................................. 348/45; 348/65
(58) Field of Classification Search
CPC ........................................................ A61B 1/00
USPC ..................................................... 348/45, 65
See application file for complete search history.

(56) References Cited

U.S. PATENT DOCUMENTS 5,258,834 A    11/1993  Tsuji et al.
5,408,265 A *   4/1995  Sasaki ............................. 348/70

FOREIGN PATENT DOCUMENTS

| JP | 04-259441 A | 9/1992 |
| JP | 06-253215 A | 9/1994 |
| JP | 2009-045113 A | 3/2009 |
| JP | 2009-072246 A | 4/2009 |
| JP | 2010-078756 A | 4/2010 |
| JP | 2011-254421 A | 12/2011 |

* cited by examiner

*Primary Examiner* — Sath V Perungavoor
*Assistant Examiner* — Jeffery Williams
(74) *Attorney, Agent, or Firm* — Scully, Scott, Murphy & Presser, P.C.

(57) ABSTRACT

An image pickup system includes an image pickup device (CIS) provided with a TG which generates a first reference synchronization signal and includes a synchronization signal self-generating counter, and a processor provided with a TG that generates a second reference synchronization signal and a reference synchronization signal comparing section that compares the first reference synchronization signal superimposed on a video signal with the second reference synchronization signal, in which when a shift occurs between the first reference synchronization signal and the second reference synchronization signal, the processor transmits the second reference synchronization signal or phase correction amount information to the CIS, and the TG changes a timing of the first reference synchronization signal according to the second reference synchronization signal or the phase correction amount information.

6 Claims, 3 Drawing Sheets

IMAGE PICKUP SYSTEM

CROSS REFERENCE TO RELATED APPLICATION

This application is a continuation application of PCT/JP2012/083452 filed on Dec. 25, 2012 and claims benefit of Japanese Application No. 2012-045824 filed in Japan on Mar. 1, 2012, the entire contents of which are incorporated herein by this reference.

BACKGROUND OF THE INVENTION

1. Field of the Invention

The present invention relates to an image pickup system including an endoscope provided with an image pickup device.

2. Description of the Related Art

In recent years, endoscopes provided with an image pickup device have been widely used in medical fields and industrial fields.

A technique for configuring an endoscope system has been known, in which a signal processing apparatus, what is called a processor, is detachably connected to an endoscope and configured to perform various kinds of signal processing related to the endoscope.

Furthermore, in such a kind of endoscope system, an example is known in which synchronization signal generation means for display control of an endoscopic image is provided on a processor side, and a generation section for generating a synchronization signal for operation of the image pickup device is disposed at a distal end portion of an endoscope insertion portion.

In this example, means for generating a synchronization signal for operation of the image pickup device disposed at the distal end portion of the endoscope insertion portion includes a function for receiving an external synchronization signal from the synchronization signal generation section on the processor side and making the internal synchronization signal follow the external synchronization signal.

In this case, a cable for connecting the synchronization signal generation means disposed at the distal end of the endoscope insertion portion and the processor has relatively long length (Regarding a transmission example of a synchronization signal, see Japanese Patent Application Laid-Open Publication No. 2009-45113).

In the above-described example, the means for generating a synchronization signal for the operation of the image pickup device is provided on the distal end portion side of the endoscope insertion portion, and another means for generating a synchronization signal, which is different from the one disposed on the distal end side of the endoscope insertion portion, is provided also in the processor.

SUMMARY OF THE INVENTION

An image pickup system according to one aspect of the present invention includes: an image pickup apparatus including: an image pickup section that outputs an electric signal after photoelectric conversion, as image information, from a plurality of pixels; a signal processing section that performs signal processing on a signal including the image information outputted from the image pickup section; a first reception section that receives a signal transmitted from outside; a first transmission section that transmits the signal processed by the signal processing section to outside; and a first reference synchronization signal generation section that generates, at a predetermined cycle, a first reference synchronization signal for the signal processing, and a processing apparatus including: a second reference synchronization signal generation section that generates, at a predetermined cycle, a second reference synchronization signal for video calculation processing with respect to the signal processed by the signal processing section; a second transmission section that is connected to the reception section in the image pickup apparatus and transmits a predetermined signal to the image pickup apparatus; a second reception section that is connected to the transmission section in the image pickup apparatus and receives a video signal on which the first reference synchronization signal is superimposed, the video signal being transmitted from the image pickup apparatus, and a reference synchronization signal comparing section that compares the first reference synchronization signal with the second reference synchronization signal, wherein the second transmission section in the processing apparatus transmits a signal related to comparison result information based on a comparison result by the reference synchronization signal comparing section to the image pickup apparatus, the first reception section in the image pickup apparatus receives the signal related to the comparison result information based on the comparison result, and the first reference synchronization signal generation section in the image pickup apparatus changes a timing of the first reference synchronization signal on the basis of the comparison result information.

DETAILED DESCRIPTION OF THE PREFERRED EMBODIMENT(S)

Hereinafter, embodiments of the present invention will be described with reference to drawings.

First Embodiment

Figure 1:
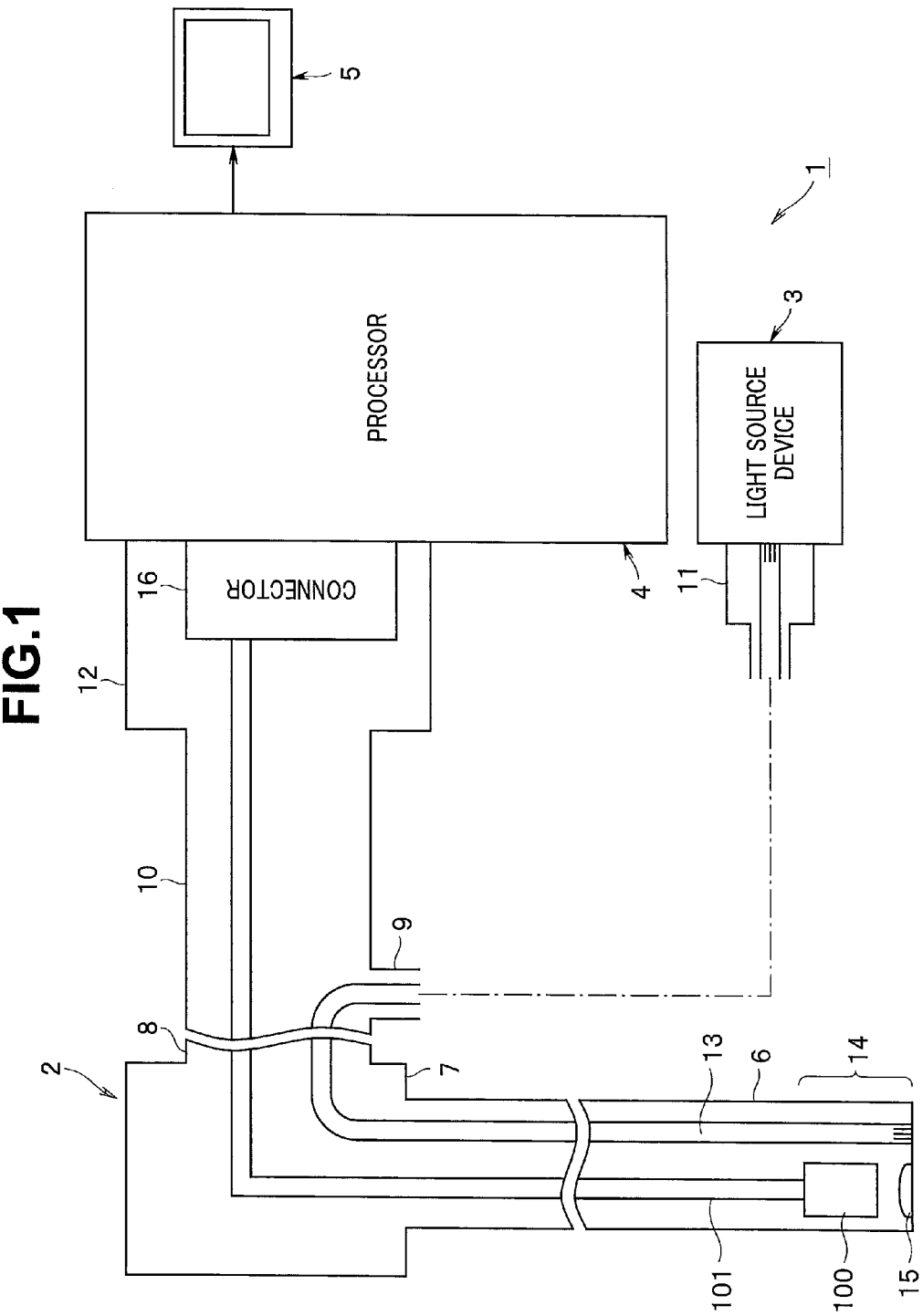
FIG. 1 illustrates an overall configuration of an image pickup system according to a first embodiment of the present invention.

As shown in FIG. 1, an image pickup system 1 according to the first embodiment of the present invention includes: an endoscope 2 provided with an image pickup device 100; a light source device 3 to which the endoscope 2 is detachably connected and which supplies illumination light to the endoscope 2; a processor 4 to which the endoscope 2 is detachably connected and which is a signal processing apparatus for performing predetermined signal processing; and a monitor 5 as a display device that displays an image signal generated by the processor 4 as an endoscopic image.

The endoscope 2 includes an elongated insertion portion 6 configured to be inserted into a body cavity, an operation portion 7 provided at a rear end of the insertion portion 6, and a universal cord 8 extended from the operation portion 7. The universal cord 8 diverges, at near a proximal end thereof or at a middle portion thereof, into a light guide cord 9 and a signal cord (signal cable) 10. A light source connector 11 located at an end portion of the light guide cord 9 is detachably connected to the light source device 3, and a signal connector 12 located at an end portion of a signal cord 10 is detachably connected to the processor 4.

A light guide 13 for transmitting illumination light is inserted inside of the insertion portion 6, the operation portion 7, and the universal cord 8. The light source connector 11 is connected to the light source device 3, thereby transmitting the illumination light from the light source device 3 by the light guide 13, and the transmitted illumination light is emitted from the distal end surface of the light guide attached to an illumination window provided at the distal end portion 14 of the insertion portion 6. Note that a connector integrally including the light source connector 11 and the signal connector 12 is connected to the light source device 3, and the signal from the signal connector 12 may be transmitted to the processor 4, through a cable connecting the light source device 3 and the processor 4.

The distal end portion 14 is provided with an observation window (image pickup window) adjacent to the illumination window, and an objective lens 15 which forms an optical image of a subject such as an illuminated diseased part is attached to the observation window. At the image-forming position of the objective lens 15, an image pickup device constituted by a CMOS image sensor (hereinafter, abbreviated as CIS) 100 is disposed, for example.

The CIS 100 is connected to a connector 16 provided inside the signal connector 12 through a general coaxial cable 101 inserted through inside the insertion portion 6 and the universal cord 8, and the connector 16 is detachably connected to the processor 4.

The processor 4 includes: a power source circuit, not shown, for generating power of a plurality of power-supply voltages necessary for the operation of the image pickup device and the like; a signal processing circuit (not shown in FIG. 1) for performing a predetermined signal processing on the image pickup signal outputted from the image pickup device, and a control circuit (not shown in FIG. 1) for controlling the power source circuit, the signal processing circuit, and the like.

Figure 2:
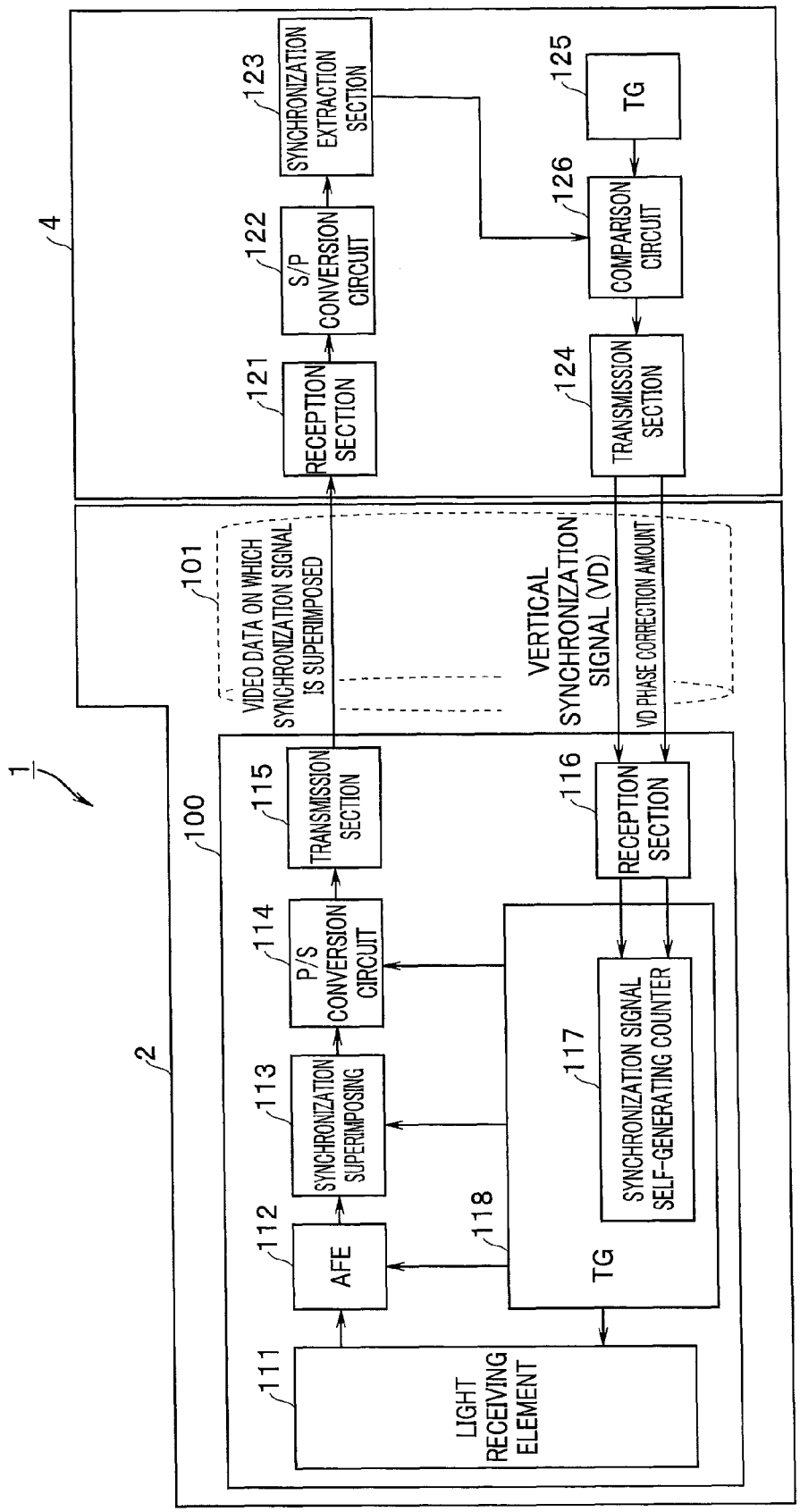
FIG. 2 illustrates a configuration of an electric system in the image pickup system according to the first embodiment.

FIG. 2 is a block diagram illustrating a configuration of an electric system in the image pickup system according to the present embodiment.

The image pickup device (CIS) 100 according to the present embodiment is constituted by what is called a CMOS (Complementary Metal-Oxide Semiconductor) image sensor, and includes: a light receiving element 111 arranged at the image-forming position of the objective lens 15; an AFE (analog front end) 112 for removing noise from a signal outputted from the light receiving element 111 and dizitizing the signal; a synchronization superimposing circuit 113 for superimposing a synchronization signal on a video signal which is an output signal from the AFE 112; a P/S conversion circuit 114 for converting the video signal into a serial signal for transmission so as to output the serial signal outside; a transmission section 115 for outputting the serial signal outside; a reception section 116 for receiving a vertical synchronization signal (VD) and the like from the external processor 4, for example; a timing generator (TG) 118 which generates a self-synchronization signal in the CIS 100 and includes a synchronization signal self-generating counter 117 that can change the self-synchronization signal on the basis of external information (vertical synchronization signal (VD) or information on phase correction amount of the vertical synchronization signal VD received from the processor 4) received by the reception section 116, the timing generator being configured to supply various kinds of synchronization signals in the CIS 100 to each of the circuits on the basis of the synchronization signal from the synchronization signal self-generating counter 117.

Note that, in the present embodiment, the synchronization signal generated by the timing generator (TG) 118 is defined as a first reference synchronization signal.

On the other hand, the processor 4 includes: a reception section 121 that receives the video signal (serial signal) including the video data transmitted from the CIS 100; an S/P conversion circuit 122 that converts the video signal (serial signal) on which the synchronization signal is superimposed and which is received by the reception section 121 into a parallel signal; a synchronization extraction section 123 that extracts a synchronization signal (that is, the synchronization signal in the CIS 100) from the received video signal on which the synchronization signal is superimposed; a timing generator (TG) 125 that generates a vertical synchronization signal (VD) for image processing in the processor 4 and supplies the generated vertical synchronization signal to various circuits; a comparison circuit 126 that compares the vertical synchronization signal (VD) in the processor 4, which is supplied from the timing generator 125, with the synchronization signal in the CIS 100, which is extracted by the synchronization extraction section 123; and a transmission section 124 that transmits information on the comparison result in the comparison circuit 126 (description will be made later on the information on the comparison result) to the CIS 100.

Note that, in the present embodiment, the synchronization signal generated in the timing generator (TG) 125 is defined as a second reference synchronization signal.

In addition, though not shown, in addition to the above-described circuits, the processor 4 includes circuits such as a power source circuit, not shown, for generating power of a plurality of power-supply voltages necessary for the operation of the image pickup device and the like, a signal processing circuit that performs predetermined signal processing for image display, and a control circuit for controlling the power source circuit, the signal processing circuit, and the like.

The general coaxial cable 101 extends from the output end of the CIS 100 in the insertion portion 6 and further passes through inside the universal cord 8, to be detachably connected to the processor 4 through the connector 16 provided inside the signal connector 12.

The general coaxial cable 101 is a cable for connecting the CIS 100 and the processor 4 through which the power supplied to the CIS 100 is transmitted, and the video signal (serial signal) on which the synchronization signal is superimposed and which is transmitted from the CIS 100, the vertical synchronization signal (VD) or information on the phase correction amount of the vertical synchronization signal VD transmitted from the processor 4, and the like are transmitted and received.

In addition, the general coaxial cable 101 is shielded by a shield member formed by an exterior member of the insertion portion 6. Furthermore, the shield member is electrically connected to a shield member formed by an exterior member of the operation portion 7, a shield member formed by an exterior member of the universal cord 8, a shield member of the signal connector 12, and the like.

As described above, in the present embodiment, the CIS 100 includes inside thereof the means (the synchronization signal self-generating counter 117 and the timing generator (TG) 118) for generating a self-synchronization signal (vertical synchronization signal (VD)), and the processor 4 connected to the CIS 100 through the general coaxial cable 101 also includes the means (timing generator (TG) 125) for mainly generating a synchronization signal of the video display system.

That is, in the present embodiment, at the distal end side of the endoscope insertion portion, the means for generating a self-synchronization signal (first reference synchronization signal) for operation of the image pickup device is provided, and also the processor 4, which is connected to the image pickup device through the general coaxial cable 101 so as to be apart from the image pickup device by a relatively long distance, is also provided with the means for generating another synchronization signal (second reference synchronization signal) which is different from the one generated on the distal end side of the endoscope insertion portion. Therefore, there is a possibility that a phase shift may occur between the synchronization signal superimposed on the video signal on the endoscope side and the synchronization signal generated on the processor 4 side.

The present invention reduces an influence of the above-described phase shift with means for solving the problem as shown below.

The processor 4 receives the video signal on which the synchronization signal is superimposed and which is transmitted from the CIS 100 side in the reception section 121, performs an S/P conversion on the video signal as appropriate, and thereafter extracts the synchronization signal (first reference synchronization signal) from the video signal on which the synchronization signal is superimposed, in a synchronization extraction section 123.

After that, the processor 4 compares the vertical synchronization signal (second reference synchronization signal) in the processor 4, which is supplied from the timing generator (TG) 125, with the synchronization signal (first reference synchronization signal) in the CIS 100, which is extracted in the synchronization extraction section 123, in the comparison circuit 126.

If a predetermined phase shift (delay) occurs, the vertical synchronization signal (second reference synchronization signal) generated in the timing generator (TG) 125 is transmitted from the transmission section 124 to the CIS 100, as information on the comparison result in the comparison circuit 126.

When the CIS 100 receives the vertical synchronization signal (second reference synchronization signal) from the processor 4 in the reception section 116, the timing generator (TG) 118 performs control to make the self-generating synchronization signal follow the second reference synchronization signal in the synchronization signal self-generating counter 117 provided inside the timing generator 118.

As described above, even if a phase shift occurs between the synchronization signal superimposed on the video signal on the endoscope side and the synchronization signal generated on the processor 4 side, that is, a phase shift occurs between the first reference synchronization signal on the endoscope side and the second reference synchronization signal on the processor 4 side, the image pickup system according to the first embodiment corrects the phase shift as appropriate, thereby enabling accurate image display without causing image defect due to the phase shift.

Second Embodiment

An image pickup system according to the second embodiment of the present invention has a similar configuration as that in the first embodiment, but different in the contents of information on the comparison result transmitted from the comparison circuit 126 to the CIS 100 and the working of the synchronization signal self-generating counter 117 in the timing generator (TG) 118 in the CIS 100 which receives the above-described information, in the case where a phase shift occurs between the synchronization signal superimposed on the video signal on the endoscope side and the synchronization signal generated on the processor 4 side. Therefore, since other configurations are the same as those in the first embodiment, description thereof will be omitted here.

In the image pickup system according to the second embodiment, similarly as in the first embodiment, the processor 4 extracts the synchronization signal (first reference synchronization signal) from the video signal on which the synchronization signal is superimposed and which is transmitted from the CIS 100 side in the synchronization extraction section 123, and thereafter compares the second reference synchronization signal supplied from the timing generator (TG) 125 with the first reference synchronization signal in the CIS 100 in the comparison circuit 126.

When a predetermined phase difference (delay) occurs, the processor 4 transmits information on a phase correction amount based on the phase shift between the first reference synchronization signal and the second reference synchronization signal, as information on the comparison result in the comparison circuit 126, from the transmission section 124 to the CIS 100.

When the CIS 100 receives the information on the phase correction amount from the processor 4, the timing generator (TG) 118 corrects the timing of the self-generating synchronization signal (first reference synchronization signal) in the synchronization signal self-generating counter 117 inside the timing generator 118, in accordance with the information on the phase correction amount.

Thus, also in the image pickup system according to the second embodiment, the phase shift between the first reference synchronization signal on the endoscope side and the second reference synchronization signal on the processor 4 side is corrected as appropriate, thereby enabling accurate image display without causing image defect due to the phase shift.

Third Embodiment

Figure 3:
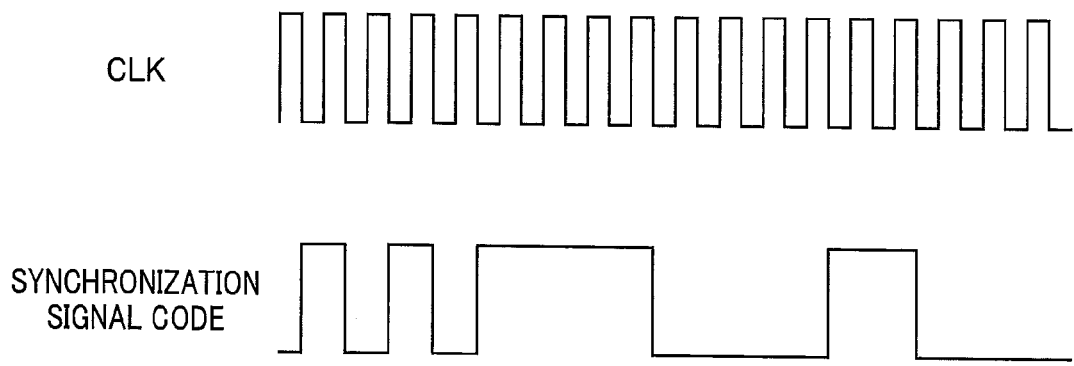
FIG. 3 illustrates an example of a synchronization signal in an image pickup system according to a third embodiment of the present invention.

FIG. 3 illustrates an example of a synchronization signal in an image pickup system according to the third embodiment of the present invention.

The main configuration of the image pickup system according to the third embodiment is similar to that of the image pickup system in the first embodiment, but ingenuity is used for the synchronization signal transmitted and received between the CIS 100 and the processor 4. Therefore, since other configurations are the same as those in the first and second embodiments, detailed description thereof will be omitted here.

As described above, the image pickup system according to the present invention includes different synchronization signal generation means on the distal end side of the endoscope insertion portion and on the processor 4 side, respectively, and the endoscope and the processor are disposed so as to be apart from each other by a relatively long distance, through the general coaxial cable 101. Furthermore, in the nature of the endoscope apparatus, the synchronization signal transmitted and received between the endoscope and the processor is exposed to an environment in which disturbance noise is likely to be applied.

On the other hand, the general coaxial cable 101 is subjected to a predetermined shielding as described above, and such shielding exhibits a certain effect also with respect to disturbance noise, or the like. However, in the third embodiment, ingenuity is used for further increasing disturbance-resistance performance.

That is, in the third embodiment, the synchronization signal transmitted and received between the CIS 100 and the processor 4, in particular, the second reference synchronization signal generated in the processor 4 and transmitted to the CIS 100 is supposed to be a signal having a synchronization detection pattern in which a plurality of bit strings each having a different bit length and a periodicity of at least one cycle are combined, as shown in FIG. 3.

The signal has such a pattern, which results in transmitting and receiving a code as if the code includes different frequency bands, thereby capable of reducing a probability of coincidence between the frequency pattern of the signal and the frequency pattern of disturbance and also reducing the influence of generation of false signal due to disturbance.

Note that in the present embodiment, the second reference synchronization signal generated in the processor 4 is taken as an example of the signal having the above-described synchronization detection pattern. However, the first reference synchronization signal generated in the CIS 100 and superimposed on the video signal may be the signal having the above-described pattern.

As described above, according to the third embodiment, it is possible to increase disturbance-resistant performance when transmitting and receiving the synchronization signal.

Fourth Embodiment

Figure 4:
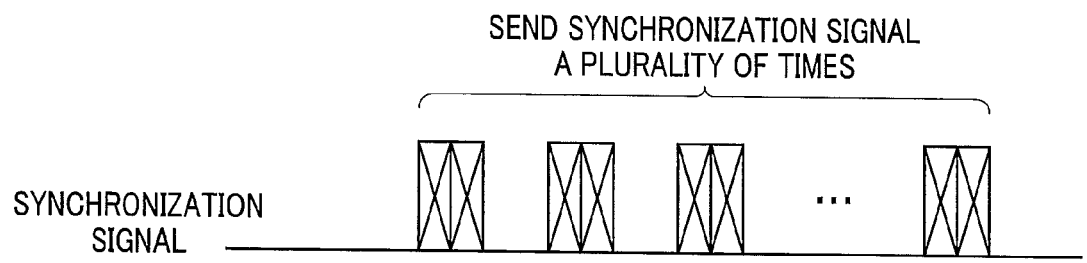
FIG. 4 illustrates a transmission example of a synchronization signal in an image pickup system according to a fourth embodiment of the present invention.

FIG. 4 illustrates a transmission example of a synchronization signal in an image pickup system according to the fourth embodiment of the present invention.

The main configuration of the image pickup system according to the fourth embodiment is similar to that in the first embodiment, as in the above-described third embodiment, but configured by using more ingenuity in the means according to the third embodiment regarding the synchronization signal transmitted and received between the CIS 100 and the processor 4, in order to further reduce the influence due to disturbance. Since other configurations are the same as those in the first to third embodiments, detailed description thereof will be omitted here.

As also described in the description of the third embodiment, in the image pickup system according to the present invention, the synchronization signal transmitted and received between the CIS 100 and the processor 4 is exposed to an environment in which disturbance noise or the like is likely to be applied.

The fourth embodiment of the present invention has a feature in that, when a synchronization signal is transmitted from the processor 4 to the CIS 100, "a signal having a synchronization detection pattern in which a plurality of bit strings each having a different bit length and a periodicity of at least one cycle are combined" in the third embodiment is intermittently transmitted a plurality of times.

The signal having the above-described synchronization detection pattern is thus transmitted a plurality of times, thereby enabling the influence due to disturbance, more particularly a loss of the signal itself by the disturbance, to be reduced as much as possible.

Note that, in the above-described embodiment, the image pickup system including, in the CMOS image sensor, the means which is disposed at the distal end of the endoscope insertion portion and which generates the synchronization signal for image pickup control is taken as an example. However, the present invention is not limited to such an image pickup system but may be applied to an image pickup system including an endoscope in which what is called CCD is disposed at the distal end of the endoscope insertion portion and means for generating the synchronization signal for image pickup control is disposed in the vicinity of the CCD, for example.

In addition, the present invention is not limited to the above-described embodiments, various changes and modifications are possible in a range without changing the gist of the present invention, and an embodiment constituted by partly combining the above-described embodiments also belongs to the present invention.

What is claimed is:
1. An image pickup system comprising:
   an image pickup apparatus including:
      an image pickup section that outputs an electric signal after photoelectric conversion, as image information, from a plurality of pixels;
      a signal processing section that performs signal processing on a signal including the image information outputted from the image pickup section;
      a first reception section that receives a signal transmitted from outside;
      a first transmission section that transmits the signal processed by the signal processing section to outside; and
      a first reference synchronization signal generation section that generates, at a predetermined cycle, a first reference synchronization signal for the signal processing, and
   a processing apparatus including:
      a second reference synchronization signal generation section that generates, at a predetermined cycle, a second reference synchronization signal for video calculation processing with respect to the signal processed by the signal processing section;
      a second transmission section that is connected to the reception section in the image pickup apparatus and transmits a predetermined signal to the image pickup apparatus;
      a second reception section that is connected to the transmission section in the image pickup apparatus and receives a video signal on which the first reference synchronization signal is superimposed, the video signal being transmitted from the image pickup apparatus, and
      a reference synchronization signal comparing section that compares the first reference synchronization signal with the second reference synchronization signal,
   wherein the second transmission section in the processing apparatus transmits a signal related to comparison result information based on a comparison result by the reference synchronization signal comparing section to the image pickup apparatus,
   the first reception section in the image pickup apparatus receives the signal related to the comparison result information based on the comparison result, and
   the first reference synchronization signal generation section in the image pickup apparatus changes a timing of the first reference synchronization signal on the basis of the comparison result information.
2. The image pickup system according to claim 1, wherein, when a shift between the second reference synchronization signal and the first reference synchronization signal is equal to or larger than a predetermined value, the second transmission section transmits the second reference syn- chronization signal, as the comparison result information, to the image pickup apparatus, according to the comparison result, and the first reference synchronization signal generation section changes the timing of the first reference synchronization signal on the basis of the comparison result information, and corrects the shift.

3. The image pickup system according to claim 1, wherein, when a shift between the second reference synchronization signal and the first reference synchronization signal is equal to or larger than a predetermined value, the second transmission section transmits the second reference synchronization signal, as the comparison result information, to the image pickup apparatus, according to the comparison result, and the first reference synchronization generation section changes the timing of the first reference synchronization signal so as to follow the second reference synchronization signal, and corrects the shift.

4. The image pickup system according to claim 1, wherein, when a shift between the second reference synchronization signal and the first reference synchronization signal is equal to or larger than a predetermined value, the second transmission section transmits phase correction information according to the comparison result, as the comparison result information, to the image pickup apparatus, and the first reference synchronization signal generation section changes the timing of the first reference synchronization signal on the basis of the phase correction information, and corrects the shift.

5. The image pickup system according to claim 1, wherein at least one of the first reference synchronization signal generation section and the second reference synchronization signal generation section generates a signal having a synchronization detection pattern in which a plurality of bit strings each having a different bit length and a periodicity of at least one cycle are combined.

6. The image pickup system according to claim 5, wherein at least one of the first reference synchronization signal generation section and the second reference synchronization signal generation section generates the synchronization detection pattern a plurality of times.

* * * * *